(12) United States Patent
McGuire et al.

(10) Patent No.: US 8,697,011 B2
(45) Date of Patent: Apr. 15, 2014

(54) SAMPLING DEVICE WITH IMMISCIBLE FLUID SUPPLY TUBE IN COUNTER-FLOW ARRANGEMENT

(75) Inventors: David McGuire, Limerick (IE); Kieran Curran, Limerick (IE); Julie Garvey, Limerick (IE); Damian Curtain, Limerick (IE)

(73) Assignee: Stokes Bio Limited, Limerick (IE)

(*) Notice: Subject to any disclaimer, the term of this patent is extended or adjusted under 35 U.S.C. 154(b) by 407 days.

(21) Appl. No.: 12/468,367

(22) Filed: May 19, 2009

(65) Prior Publication Data

US 2010/0294048 A1 Nov. 25, 2010

(51) Int. Cl.
*B01L 3/02* (2006.01)

(52) U.S. Cl.
USPC ............................ 422/510; 422/509; 422/501

(58) Field of Classification Search
None
See application file for complete search history.

(56) References Cited

U.S. PATENT DOCUMENTS

| | | | |
|---|---|---|---|
| 2,398,234 A | | 4/1946 | Long |
| 4,259,291 A | * | 3/1981 | Smythe ............................ 422/82 |
| 4,318,885 A | | 3/1982 | Suzuki et al. |
| 4,357,301 A | | 11/1982 | Cassaday et al. |
| 4,574,850 A | * | 3/1986 | Davis ................................ 141/9 |
| 4,984,475 A | | 1/1991 | Uffenheimer et al. |
| 5,270,183 A | | 12/1993 | Corbett et al. |
| 5,720,923 A | | 2/1998 | Haff et al. |
| 5,779,977 A | | 7/1998 | Haff et al. |
| 5,827,480 A | | 10/1998 | Haff et al. |
| 6,033,880 A | | 3/2000 | Haff et al. |
| 2007/0039866 A1 | | 2/2007 | Schroeder et al. |
| 2007/0062583 A1 | | 3/2007 | Cox et al. |
| 2007/0068573 A1 | | 3/2007 | Cox et al. |
| 2007/0141593 A1 | | 6/2007 | Lee et al. |
| 2010/0304443 A1 | | 12/2010 | Davies et al. |

FOREIGN PATENT DOCUMENTS

| | | |
|---|---|---|
| EP | 0188265 | 7/1986 |
| GB | 2122744 | 1/1984 |
| GB | 2453585 | 4/2009 |
| JP | 7095013 | 10/1995 |
| WO | WO 03/016558 | 2/2003 |
| WO | 2007/024800 | 3/2007 |
| WO | 2010/133965 | 11/2010 |

OTHER PUBLICATIONS

Litborn, Erik et al. "Liquid lid for biochemical reactions in chip-based nanovials." Journal of Chromatography B (2000) 137-147.*
Sjodahl, Johan et al. "Chip with Twin Anchors for Reduced Ion Suppression and Improved Mass Accuracy in MALDI-TOF Mass Spectrometry." Analytical Chemistry (2005) 77 827-832.*
International Search Report and Written Opinion for PCT/IB2010/01333 mailed Mar. 31, 2011.
International Search Report and The Written Opinion for International Application No. PCT/US2011/030073 dated Dec. 13, 2011.

* cited by examiner

*Primary Examiner* — Christopher A Hixson (57) ABSTRACT

The present invention generally relates to devices, systems, and methods for acquiring and/or dispensing a sample without introducing a gas into a microfluidic system, such as a liquid bridge system. An exemplary embodiment provides a sampling device including: a sampling member for acquiring or dispensing a sample; and a supply of a fluid that is immiscible with the sample; in which the device is configured to provide a continuous flow of immiscible fluid enveloping the sampling member.

13 Claims, 4 Drawing Sheets

Panel E

SAMPLING DEVICE WITH IMMISCIBLE FLUID SUPPLY TUBE IN COUNTER-FLOW ARRANGEMENT

FIELD OF THE INVENTION

The present invention generally relates to devices, systems, and methods for acquiring and/or dispensing a sample without introducing a gas into a microfluidic system, such as a liquid bridge system.

BACKGROUND

Microfluidics is a technology involving micro-scale devices that handle small volumes of fluids, e.g., microliter, nanoliter, picoliter, or femtoliter volumes. Because microfluidics can accurately and reproducibly control and dispense small volumes of fluid, in particular volumes less than 1 µl, application of microfluidics provides significant cost-savings. The use of microfluidics technology reduces cycle times, shortens time-to-results, and increase throughput. Furthermore incorporation of microfluidics technology enhances system integration and automation.

An exemplary microfluidic device involves liquid bridge technology. Liquid bridge technology involves sample droplet formation utilizing immiscible fluids. A sample droplet is formed at an end of an inlet port that extends into a chamber that is filled with a carrier fluid. The carrier fluid is immiscible with the sample droplet. The sample droplet grows until large enough to span a gap to an outlet port in the chamber, forming an axisymmetric liquid bridge. By adjusting the flow rate or by introducing a second sample droplet to the first sample droplet, an unstable funicular bridge is formed that subsequently ruptures from the inlet port. After rupturing from the inlet port, the sample droplet enters the outlet port, surrounded by the carrier fluid from the chamber. The process then repeats itself.

Given the small dimensions of microfluidic systems that utilize liquid bridge technology, introduction of gas into the system presents significant operation problems. The most common cause of gas introduction into a liquid bridge system is during sample acquisition, i.e., interaction between a sample tip and a vessel for acquiring the sample and introducing the sample into the system. Once gas is introduced into the system, the system needs to be shutdown and purged to remove the gas. Purging the system and re-equilibrating the system for operation wastes time and valuable resources.

There is an unmet need for devices and systems that can acquire a sample and interface with a system without introducing a gas into the system.

SUMMARY

The present invention generally relates to devices, systems, and methods for acquiring and/or dispensing a sample without introducing a gas into a microfluidic system, such as a liquid bridge system. Devices and systems of the invention accomplish sample acquisition without introduction of a gas by utilizing counter-flow principles, thus providing a continuous flow of immiscible fluid to envelop a sampling member. Accordingly, the invention provides sample acquisition devices that can interact with a vessel to introduce a sample into a microfluidic system, e.g., a liquid bridge system, without introducing gas into the system, thus avoiding the detrimental effects that a gas has on a microfluidic system. Sampling devices and systems of the invention improve microfluidic system efficiency by eliminating system downtime that is involved with purging the microfluidic system to remove unwanted gas, and re-equilibrating the system for operation.

Numerous configurations of devices and systems that accomplish sample acquisition and/or dispensing without introduction of a gas are provided herein. One configuration of a sampling device includes: a sampling member for acquiring or dispensing a sample; and a supply of a fluid that is immiscible with the sample; in which the device is configured to provide a continuous flow of immiscible fluid enveloping the sampling member. In this configuration, there is counter-flow of the immiscible fluid from an exterior of the sampling member to an interior of the sampling member.

The device can be configured for sample acquisition by flowing the immiscible fluid down an exterior of the sampling member, and taking in the immiscible fluid up an interior of the sampling member. The device can be configured for sample dispensing by flowing the immiscible fluid down an interior and an exterior of the sampling member.

Another configuration of a sampling device includes: an outer sheath; and a plurality of tubes within the sheath, in which at least one of the tubes acquires a sample, and at least one of the tubes expels a fluid that is immiscible with the sample, wherein the at least one tube that acquires the sample is extendable beyond a distal end of the sheath and retractable to within the sheath. In this configuration, a distal portion of the outer sheath is filled with the immiscible fluid, continuously immersing the distal portion of the tube that acquires the sample in the immiscible fluid.

In this configuration, there is counter-flow of the immiscible fluid between the tube that expels the immiscible fluid and the tube that acquires the sample. For example, the immiscible fluid is continuously expelled from the tube that expels the immiscible fluid, and the immiscible fluid is continuously taken in by the tube that acquires the sample. The outer sheath of the device is configured to interact with a vessel, and the tube that acquires the sample is configured to interact with the sample in the vessel.

Devices of the invention can be configured to be detachable from, and adapted for coupling to, a pipette head of a pipette. Devices of the invention can be configured to be detachable from, and adapted for coupling to, a pipette head attachment assembly of an autopipettor. Devices of the invention can be configured to operate in fluid contact with a liquid bridge system.

An exemplary system for sample acquisition includes: a sampling member; a vessel for containing a sample and an overlay of a fluid that is immiscible with the sample; in which a distal end of the sampling member is configured such that it is not removed above the immiscible overlay between sample acquisitions. When the sampling member needs to be removed from the vessel so that the vessel can be removed from the system and another vessel can be inserted, the system continuously expels immiscible fluid from the sampling member as the sampling member is extracted from the vessel and as the sampling member remains extracted from the vessel. Thus the sampling member does not take in a gas during sample acquisition, between sample acquisitions, and between vessel changes.

The system can further include a robotics system that controls movement of the sampling tube and a pump connected to the sampling member. The system can also further include a liquid bridge that is in fluid contact with the sampling member, a thermocycler, and a detection system, such as an optics system.

Another exemplary system for sample acquisition includes: a sampling device including an outer sheath and a plurality of tubes within the sheath, in which at least one of the tubes acquires a sample, and at least one of the tubes expels a fluid that is immiscible with the sample, wherein the at least one tube that acquires the sample is extendable beyond a distal end of the sheath and retractable to within the sheath; and a vessel for containing a sample and an overlay of a fluid that is immiscible with the sample; in which a distal end of the outer sheath and the tube that acquires the sample are configured to interact with the vessel to acquire the sample without also acquiring a gas.

The system can further include a robotics system that controls movement of the sampling device, and controls movement of the sample acquisition tube. The system can further include a first pump connected to the sample acquisition tube, and a second pump connected to the at least one tube that expels the immiscible fluid. The system can also further include a liquid bridge that is in fluid contact with the sampling tube, a thermocycler, and a detection system, such as an optics system.

The vessel can be a plate, for example a 96 well or 384 well microtiter plate. The sample can be any chemical or biological species. Certain samples include genetic material. Other samples can include PCR reagents. The immiscible fluid is chosen based on the nature of the sample. If the sample is hydrophilic in nature, the immiscible fluid chosen is a hydrophobic fluid. An exemplary hydrophobic fluid is oil, such as silicone oil. If the sample is hydrophobic in nature, the immiscible fluid chosen is a hydrophilic fluid.

The invention also provides a method for acquiring a sample including: contacting a sampling member to a vessel containing a sample, in which the sampling member is enveloped in a fluid that is immiscible with the sample; and acquiring the sample from the vessel, in which the sample is acquired without the introduction of a gas into the sampling member. The method utilizes counter-flow of the immiscible fluid. For example, the immiscible fluid flows down an exterior of the sampling member, and is taken up an interior of the sampling member.

The method can further include, flowing the sample to a liquid bridge, flowing the sample to a thermocycler, analyzing the sample, or performing PCR on the sample.

These and other aspects, features, and benefits according to the invention will become clearer by reference to the drawings described below and also the description that follows.

DETAILED DESCRIPTION

The present invention generally relates to devices, systems, and methods for acquiring and/or dispensing a sample without introducing a gas into a microfluidic system, such as a liquid bridge system. Numerous configurations of devices and systems that accomplish sample acquisition and/or dispensing without introduction of a gas into a microfluidic system are provided herein.

Figure 1:
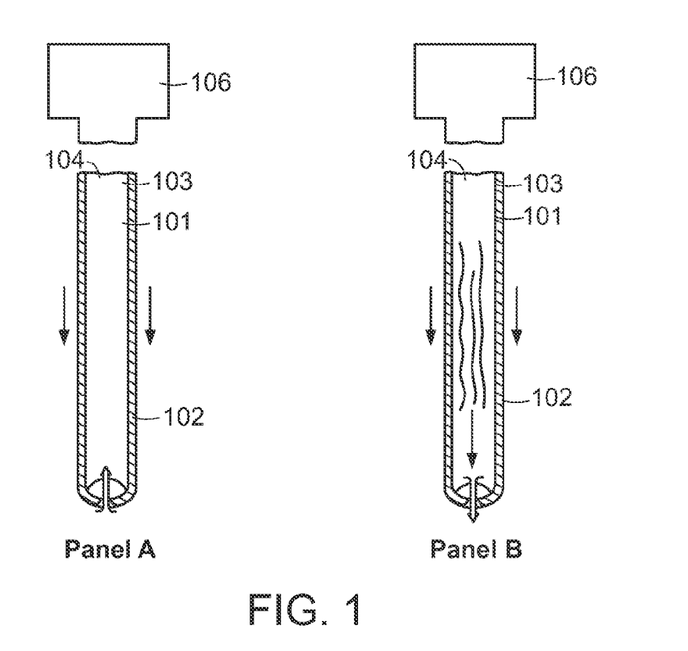
FIG. 1 is an embodiment of a sampling device, panel A showing sample acquisition and panel B showing sample dispensing.

FIG. 1 shows a configuration of a sampling device 100 for sample acquisition and/or dispensing without introduction of gas into a microfluidic system, e.g., a liquid bridge system. The sampling device 100 includes a sampling member 101 for acquiring (FIG. 1, panel A) or dispensing (FIG. 1, panel B) a sample. A sampling member refers to any type of device used to acquire and/or dispense a sample. Exemplary sampling members include tubes, channels, capillaries, pipette tips, or probes. The sampling member can be of any shape, for example, a cylinder, a regular polygon, or an irregular polygon. The sampling member can be made of any material suitable to interact with biological or chemical species. Exemplary materials include TEFLON (commercially available from Dupont, Wilmington, Del.), polytetrafluoroethylene (PTFE; commercially available from Dupont, Wilmington, Del.), polymethyl methacrylate (PMMA; commercially available from TexLoc, Fort Worth, Tex.), polyurethane (commercially available from TexLoc, Fort Worth, Tex.), polycarbonate (commercially available from TexLoc, Fort Worth, Tex.), polystyrene (commercially available from TexLoc, Fort Worth, Tex.), polyetheretherketone (PEEK; commercially available from TexLoc, Fort Worth, Tex.), perfluoroalkoxy (PFA; commercially available from TexLoc, Fort Worth, Tex.), or fluorinated ethylene propylene (FEP; commercially available from TexLoc, Fort Worth, Tex.).

Sampling device 100 further includes a supply of a fluid 106 that is immiscible with the sample. The supply of fluid can be directly coupled to the sampling member. Alternatively, the supply of fluid can be indirectly coupled to the sampling member, such as by tubing or channels. Determination of the fluid to be used is based on the properties of the sample. If the sample is a hydrophilic sample, the fluid to used should be a hydrophobic fluid. An exemplary hydrophobic fluid is oil, such as AS100 silicone oil (commercially available from Union Carbide Corporation, Danbury, Conn.). Alternatively, if the sample is a hydrophobic sample, the fluid to used should be a hydrophilic fluid. One of skill in the art will readily be able to determine the type of fluid to be used based on the properties of the sample.

Sample device 100 is configured to provide a continuous flow of immiscible fluid 102 enveloping the sampling member 101. This is accomplished by utilizing counter-flow between the exterior 103 of the sampling member 101 and the interior 104 of the sampling member 101. FIG. 1, panel A is a drawing depicting an embodiment in which there is counter-flow of the immiscible fluid 102 from an exterior 103 of the sampling member 101 to an interior 104 of the sampling member 101. In this configuration, the device can be utilized for sample acquisition. FIG. 1, panel B is a drawing depicting an embodiment in which the device 100 is configured for sample dispensing by flowing the immiscible fluid 102 down an interior 104 and an exterior 103 of the sampling member 101.

Flow rates of the immiscible fluid are controlled by a fluid controller, e.g., a PC running WinPumpControl software (Open Cage Software, Inc., Huntington, N.Y.), connected to at least one pump. An exemplary pump is shown in Davies et al. (WO 2007/091229). Other commercially available pumps can also be used. Exemplary flow rates range from about 1 µl/min to about 100 µl/min. An exemplary flow rate is about 1 µl/min, 3 µl/min, 5 µl/min, 10 µl/min, 20 µl/min, 30 µl/min, 50 µl/min, 70 µl/min, 90 µl/min, 95 µl/min, or about 100 µl/min. In certain embodiments, the flow rate of immiscible fluid 102 down the exterior 103 of the sampling member 101 is similar to or the same as the flow rate of the immiscible fluid 102 up the interior 104 of the sampling member 101. In certain embodiments, the flow rate of immiscible fluid 102 down the exterior 103 of the sampling member 101 is slightly greater than the flow rate of the immiscible fluid 102 up the interior 104 of the sampling member 101. For example, the flow rate of immiscible fluid 102 down the exterior 103 of the sampling member 101 is about 10 µl/min, while the flow rate of the immiscible fluid 102 up the interior 104 of the sampling member 101 is about 8 µl/min. Because the flow rate of the immiscible fluid 102 down the exterior 103 of the sampling member 101 is about the same as or greater than the flow rate of the immiscible fluid 102 up the interior 104 of the sampling member 101, the sampling member 101 is continuously enveloped by the immiscible fluid 102. Therefore, the sampling member 101 can acquire a sample without introduction of a gas into a microfluidic system, e.g., a liquid bridge system.

Figure 2:
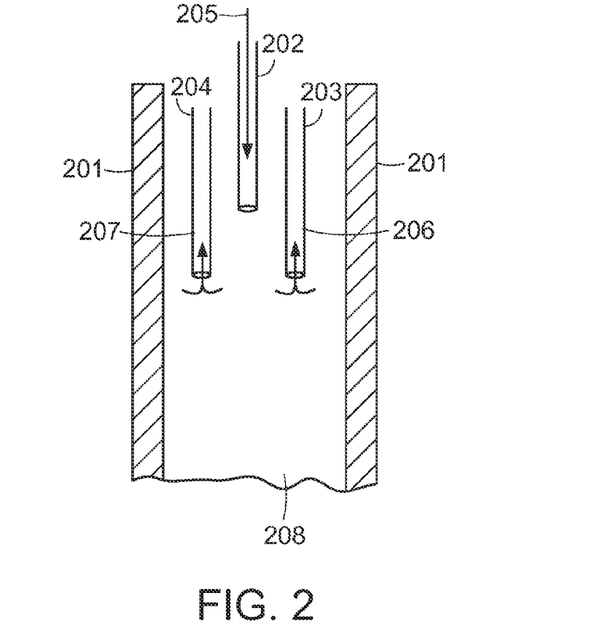
FIG. 2 is another embodiment of a sampling device.

FIG. 2 shows a configuration of a sampling device 200 for sample acquisition and/or dispensing without introduction of gas into a microfluidic system, e.g., a liquid bridge system. The sampling device 200 includes an outer sheath 201; and a plurality of tubes within the sheath 201. In FIG. 2, device 200 is shown with two tubes 203 and 204 that acquire a sample. However, device 200 can be configured with only a single tube for sample acquisition, or can be configured with more than two tubes for sample acquisition, e.g., 3 tubes, 4 tubes, 5 tubes, 10 tubes, 15 tubes, 20 tubes, 50 tubes, etc. In FIG. 2, device 200 is shown with one tube 202 that expels a fluid that is immiscible with the sample 205. However, device 200 can be configured with more than one tube that that expels a fluid that is immiscible with the sample, e.g., 3 tubes, 4 tubes, 5 tubes, 10 tubes, 15 tubes, 20 tubes, 50 tubes, etc. In device 200, the tubes that acquires the sample 203 and 204 are extendable beyond a distal end of the sheath and retractable to within the sheath. FIG. 2 shows the sample acquisition tubes 203 and 204 retracted within the outer sheath 201.

Figure 3:
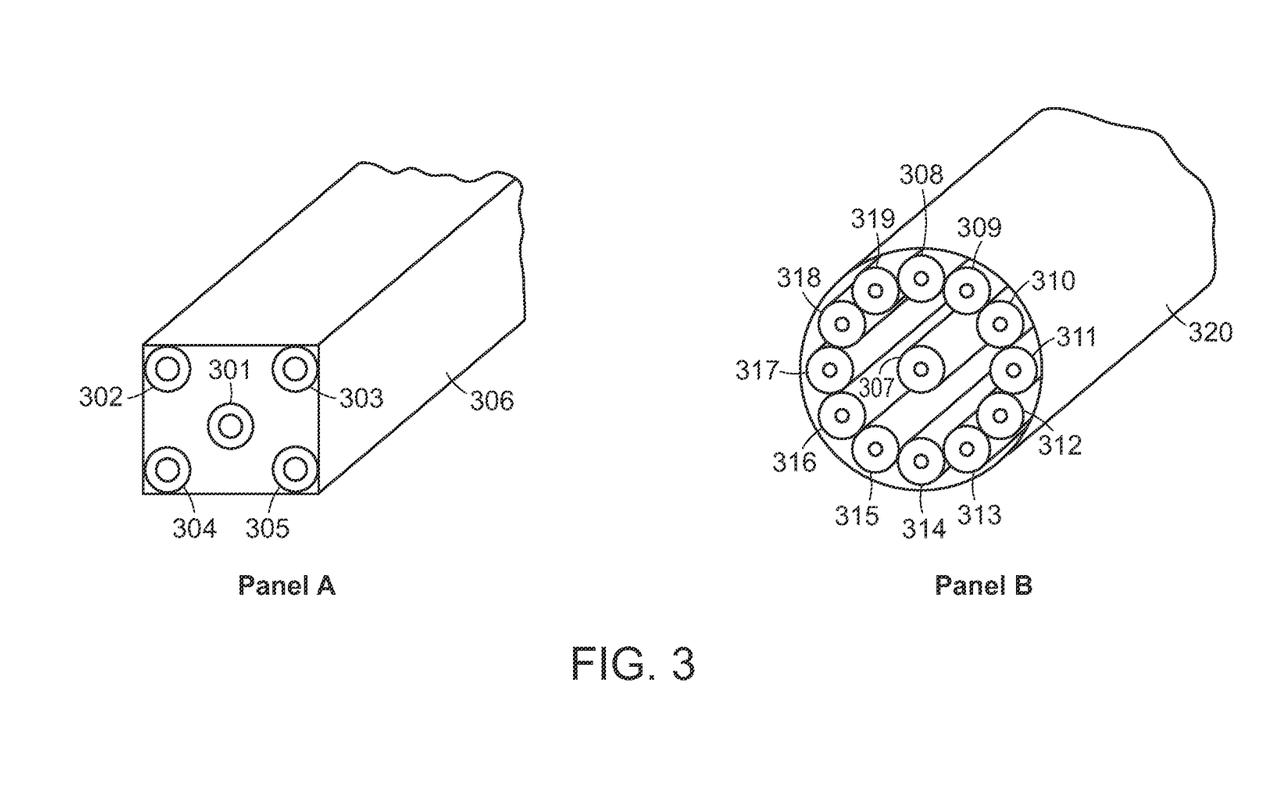
FIG. 3, panels A and B are drawings showing different configurations of tubes for the device shown in FIG. 2.

FIG. 3, panel A shows a depiction of a of sampling device 200, having a center tube 301 that expels a fluid that is immiscible with the sample, and four sample acquisition tubes 302 to 305 within outer sheath 306. FIG. 3, panel B shows a depiction of a sampling device 200, having a tube 307 that expels a fluid that is immiscible with the sample that is centered around 12 sample acquisition tubes 308 to 319, within outer sheath 320. The tube that expels the immiscible fluid can have the same inner diameter and outer diameter as the sample acquisition tubes. Alternatively, the tube that expels the immiscible fluid can have a different inner diameter and a different outer diameter than the sample acquisition tubes. Exemplary dimensions of tubes 301 to 305 and 307 to 319 include an inner diameter of about 150 µm and an outer diameter of about 300 µm. The diameter of the outer sheath is dependant on the total number of tubes, and the configuration of the tubes.

The outer sheath and the plurality of tubes can be of any shape, for example, a cylinder, a regular polygon, or an irregular polygon. The shape of the outer sheath is independent of the shape of the plurality of tubes. The outer sheath and the plurality of tubes can be made of any material suitable to interact with biological or chemical species. Exemplary materials include TEFLON (commercially available from Dupont, Wilmington, Del.), polytetrafluoroethylene (PTFE; commercially available from Dupont, Wilmington, Del.), polymethyl methacrylate (PMMA; commercially available from TexLoc, Fort Worth, Tex.), polyurethane (commercially available from TexLoc, Fort Worth, Tex.), polycarbonate (commercially available from TexLoc, Fort Worth, Tex.), polystyrene (commercially available from TexLoc, Fort Worth, Tex.), polyetheretherketone (PEEK; commercially available from TexLoc, Fort Worth, Tex.), perfluoroalkoxy (PFA; commercially available from TexLoc, Fort Worth, Tex.), or Fluorinated ethylene propylene (FEP; commercially available from TexLoc, Fort Worth, Tex.).

Device 200 utilizes counter-flow between the tube 202 that continuously expels a fluid that is immiscible with the sample 205, and sample acquisition tubes 203 and 204 that continuously take in immiscible fluid 205. Flow rates of the immiscible fluid are controlled by a fluid controller, e.g., a PC running WinPumpControl software (Open Cage Software, Inc., Huntington, N.Y.), connected to at least one pump. An exemplary pump is shown in Davies et al. (WO 2007/091229). Other commercially available pumps can also be used. Exemplary flow rates range from about 1 µl/min to about 100 µl/min. An exemplary flow rate is about 1 µl/min, 3 µl/min, 5 µl/min, 10 µl/min, 20 µl/min, 30 µl/min, 50 µl/min, 70 µl/min, 90 µl/min, 95 µl/min, or about 100 µl/min.

In certain embodiments, flow is controlled such that the flow rate out of the tube 202 that continuously expels the immiscible fluid 205 is the same or similar to the total intake flow rate of sample acquisition tubes 203 and 204. For example, the flow rate out of tube 202 can range from about 2 µl/min to about 100 µl/min, while the intake flow rate for each of sample acquisition tubes 203 and 204 can range from about 1 µl/min to about 50 µl/min. Exemplary flow rates are as follows: flow rate of 2 µl/min expelled from tube 202, with an intake flow rate for each of sample acquisition tubes 203 and 204 of 1 µl/min; flow rate of 6 µl/min expelled from tube 202, with an intake flow rate for each of sample acquisition tubes 203 and 204 of 3 µl/min; flow rate of 10 µl/min expelled from tube 202, with an intake flow rate for each of sample acquisition tubes 203 and 204 of 5 µl/min; flow rate of 20 µl/min expelled from tube 202, with an intake flow rate for each of sample acquisition tubes 203 and 204 of 10 µl/min; and flow rate of 100 µl/min expelled from tube 202, the intake flow rate for each of sample acquisition tubes 203 and 204 is 50 µl/min.

Alternatively, the flow rate out of tube 202 is greater than the total intake flow rate of sample acquisition tubes 203 and 204. For example, the flow rate out of tube 202 can range from about 5 µl/min to about 100 µl/min, while the intake flow rate for each of sample acquisition tubes 203 and 204 can range from about 1 µl/min to about 95 µl/min. Exemplary flow rates are as follows: flow rate of 6 µl/min expelled from tube 202, with an intake flow rate for each of sample acquisition tubes 203 and 204 of 2 µl/min; flow rate of 10 µl/min expelled from tube 202, with an intake flow rate for each of sample acquisition tubes 203 and 204 of 4 µl/min; flow rate of 20 µl/min expelled from tube 202, with an intake flow rate for each of sample acquisition tubes 203 and 204 of 8 µl/min; and flow rate of 100 µl/min expelled from tube 202, with an intake flow rate for each of sample acquisition tubes 203 and 204 of 48 µl/min. In this regard, a slightly greater amount of immiscible fluid is expelled into the outer sheath than is taken in by the sample acquisition tubes. Thus, a lower portion of the outer sheath 208 is continuously filled with the immiscible fluid 205, and distal portions 206 and 207 of sample acquisition tubes 203 and 204 are continuously immersed in the immiscible fluid.

The devices of the invention can be configured to be detachable from, and adapted for coupling to, a pipette head of a pipette. The devices of the invention can be configured to be detachable from, and adapted for coupling to, a pipette head attachment assembly of an autopipettor.

Figure 4:
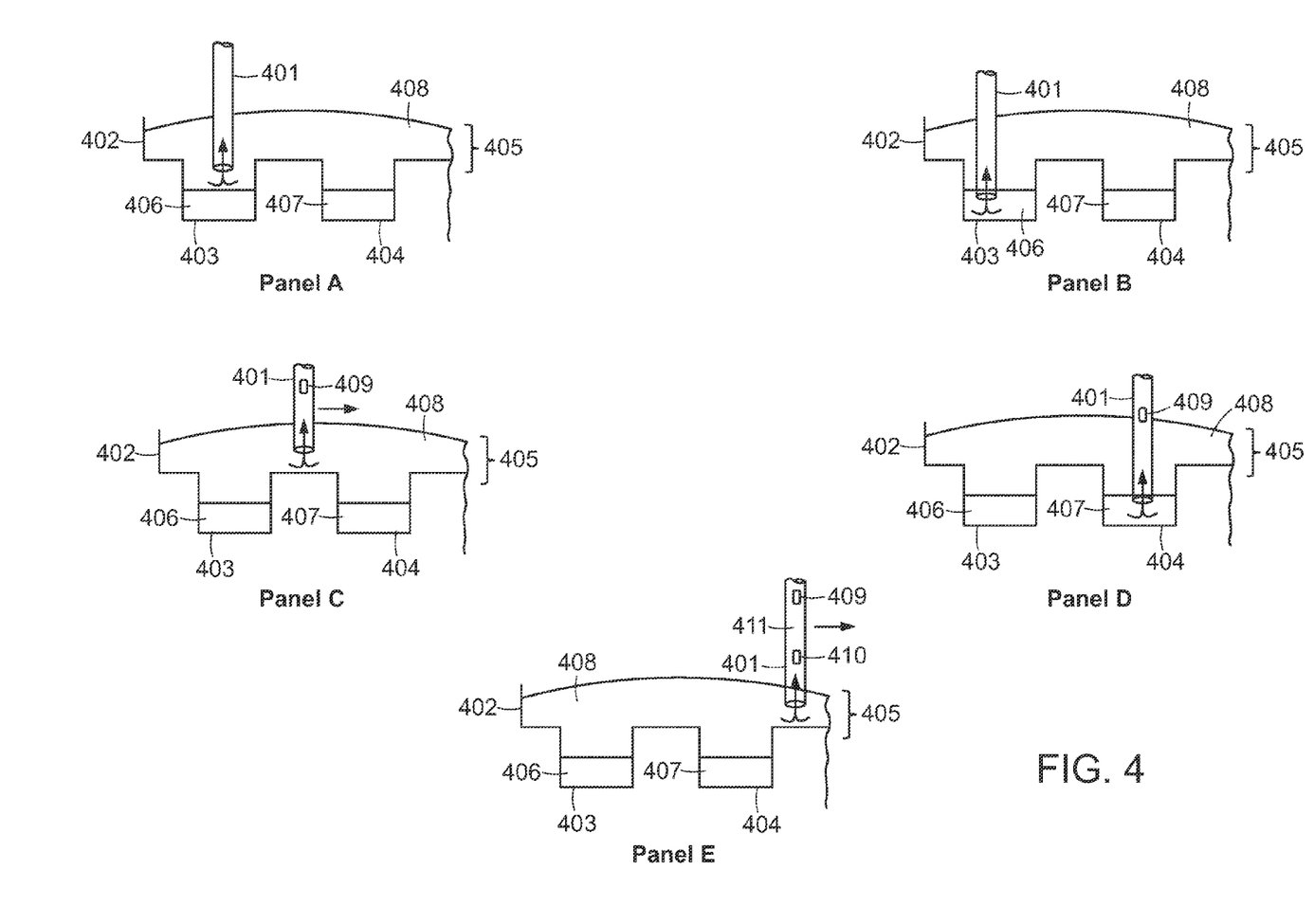
FIG. 4, panels A to E are drawings depicting an embodiment of a system having a sampling member and a vessel, and also depict interaction of the sampling member and the vessel.

FIG. 4 depicts a system 400 including a sampling member 401 and a vessel 402, and shows interaction of the sampling member 401 and the vessel 402 for acquisition of samples. The vessel 402, can be any type of vessel that is suitable for holding a sample. Exemplary vessels include plates (e.g., 96 well or 384 well plates), eppendorf tubes, vials, beakers, flasks, centrifuge tubes, capillary tubes, cryogenic vials, bags, cups, or containers. The vessel can be made of any material suitable to interact with biological or chemical species. Exemplary materials include TEFLON (commercially available from Dupont, Wilmington, Del.), polytetrafluoroethylene (PTFE; commercially available from Dupont, Wilmington, Del.), polymethyl methacrylate (PMMA; commercially available from TexLoc, Fort Worth, Tex.), polyurethane (commercially available from TexLoc, Fort Worth, Tex.), polycarbonate (commercially available from TexLoc, Fort Worth, Tex.), polystyrene (commercially available from TexLoc, Fort Worth, Tex.), polyetheretherketone (PEEK; commercially available from TexLoc, Fort Worth, Tex.), perfluoroalkoxy (PFA; commercially available from TexLoc, Fort Worth, Tex.), or Fluorinated ethylene propylene (FEP; commercially available from TexLoc, Fort Worth, Tex.).

In this figure, the vessel is a plate. The plate has wells 403 and 404, and side walls that extend above the top of each well, forming a recessed area 405 within the plate. The bottom portion of each well is filled with samples 406 and 407, and the remaining portion of each well 406 and 407 along with the recessed area 405 is filled with an overlay of a fluid that is immiscible with the sample 408.

The system is primed by flowing the immiscible fluid out of sampling member 401, until sampling member 401 is inserted into the overlay of immiscible fluid 408. Once sampling member 401 is inserted into the overlay of immiscible fluid 408, system pumps reverse the flow of immiscible fluid, and the sampling member 401 takes in immiscible fluid from the overlay of immiscible fluid 408 (FIG. 4, panel A). The sampling member 401 is shown as a tube in this figure, however, the sampling member can be any device that can acquire a sample, such as a channel, a capillary, a pipette tip, or a probe. The sampling member can be of any shape, for example, a cylinder, a regular polygon, or an irregular polygon. The sampling member can be made of any material suitable to interact with biological or chemical species. Exemplary materials include TEFLON (commercially available from Dupont, Wilmington, Del.), polytetrafluoroethylene (PTFE; commercially available from Dupont, Wilmington, Del.), polymethyl methacrylate (PMMA; commercially available from TexLoc, Fort Worth, Tex.), polyurethane (commercially available from TexLoc, Fort Worth, Tex.), polycarbonate (commercially available from TexLoc, Fort Worth, Tex.), polystyrene (commercially available from TexLoc, Fort Worth, Tex.), polyetheretherketone (PEEK; commercially available from TexLoc, Fort Worth, Tex.), perfluoroalkoxy (PFA; commercially available from TexLoc, Fort Worth, Tex.), or Fluorinated ethylene propylene (FEP; commercially available from TexLoc, Fort Worth, Tex.).

Flow rates of the immiscible fluid are controlled by a fluid controller, e.g., a PC running WinPumpControl software (Open Cage Software, Inc., Huntington, N.Y.), connected to at least one pump. An exemplary pump is shown in Davies et al. (WO 2007/091229). Other commercially available pumps can also be used. Exemplary flow rates range from about 1 µl/min to about 100 µl/min. An exemplary flow rate is about 1 µl/min, 3 µl/min, 5 µl/min, 10 µl/min, 20 µl/min, 30 µl/min, 50 µl/min, 70 µl/min, 90 µl/min, 95 µl/min, or about 100 µl/min. Because intake of immiscible is at a low flow rate, for example 100 µl/min, the amount of immiscible fluid removed from the overlay of immiscible fluid 408 in vessel 402 is negligible with respect to the amount of time required to acquire each sample in the plate. In certain embodiments, the system can include a supply of immiscible fluid in fluid contact (e.g., by tubing) with the vessel 402 to replace the immiscible fluid that is taken in by the sampling member 402 from the overlay of immiscible fluid 408.

Now primed, the sampling member 401 is extended into well 403 to acquire an amount of sample 406 (FIG. 4, panel B). Samples can be any type of biological or chemical species. In certain embodiments, the sample is a gene or gene product from a biological organism. Standard scientific protocols are available for extraction and purification of mRNA and subsequent production of cDNA. In other embodiments, the sample includes PCR reagents. A typical Q-PCR reaction contains: fluorescent double-stranded binding dye, Taq polymerase, deoxynucleotides of type A, C, G, and T, magnesium chloride, forward and reverse primers and subject cDNA, all suspended within an aqueous buffer. Reactants, however, may be assigned into two broad groups: universal and reaction specific. Universal reactants are those common to every Q-PCR reaction, and include: fluorescent double-stranded binding dye, Taq polymerase, deoxynucleotides A, C, G and T, and magnesium chloride. Reaction specific reactants include the forward and reverse primers and patient cDNA.

Once a sufficient amount of sample 406 has been acquired, sampling member 401 is retracted from sample 406 in well 403 to the overlay of immiscible fluid 408 (FIG. 4, panel C). Sampling member 401 remains in the overlay of immiscible fluid 408 and continues to take in the immiscible fluid 408 (FIG. 4, panel C). Sampling member 401 proceeds to move through the recessed area 405 containing the overlay of immiscible fluid 408 to the next well 404 containing a sample 407 (FIG. 4, panel C). As sampling member 401 moves to the next well 404, acquired sample 409 continues to move through sampling member 401 (FIG. 4, panel C).

Once positioned above well 404, the sampling member 401 is extended into well 404 to acquire an amount of sample 407 (FIG. 4, panel D). Once a sufficient amount of sample 407 has been acquired, sampling member 401 is retracted from sample 407 in well 404 to the overlay of immiscible fluid 408 (FIG. 4, panel D). Sampling member 401 remains in the overlay of immiscible fluid 408 and continues to take in the immiscible fluid 408 (FIG. 4, panel D). Sampling member 401 proceeds to move through the recessed area 405 containing the overlay of immiscible fluid 408 to the next well containing a sample (FIG. 4, panel E). As sampling member 401 moves to the next well, acquired sampled 410 continues to move through sampling member 401 (FIG. 4, panel E). Acquired sample 409 and acquired sample 410 are separated by the immiscible fluid 411.

The process repeats until the desired number of samples have been acquired. Because sampling member 401 is continuously taking in immiscible fluid 408 and is not removed above the overlay of immiscible fluid 408, samples are acquired without the system taking in any gas. Because samples within a vessel or within separate vessels are separated by the immiscible fluid, there is no carry-over or cross contamination between samples in a vessel and between samples in different vessels.

The sampling member 401 is controlled by a robotics system. The robotics system controls movement of the sampling member 401 between sample wells and during sample acquisition and/or dispensing. At least one pump is connected to the sampling member 401. An exemplary pump is shown in Davies et al. (WO 2007/091229). Other commercially available pumps can also be used. The pump is controlled by a flow controller. e.g., a PC running WinPumpControl software (Open Cage Software, Inc., Huntington, N.Y.), for controlling direction of flow and flow rates. Sampling system 400 can be fluidly connected, e.g., tubes or channels, to an type of analysis device. In certain embodiments, the sampling system 400 is connected to a liquid bridge system, as shown in Davies et al. (WO 2007/091228). The liquid bridge system can be connected to a thermocycler to perform PCR reactions on the acquired sample. An exemplary thermocycler and methods of fluidly connecting a thermocycler to a liquid bridge system are shown in Davies et al. (WO 2005/023427, WO 2007/091230, and WO 2008/038259). The thermocycler can be connected to an optical detecting device to detect the products of the PCR reaction. An optical detecting device and methods for connecting the device to the thermocycler are shown in Davies et al. (WO 2007/091230 and WO 2008/038259).

Figure 5:
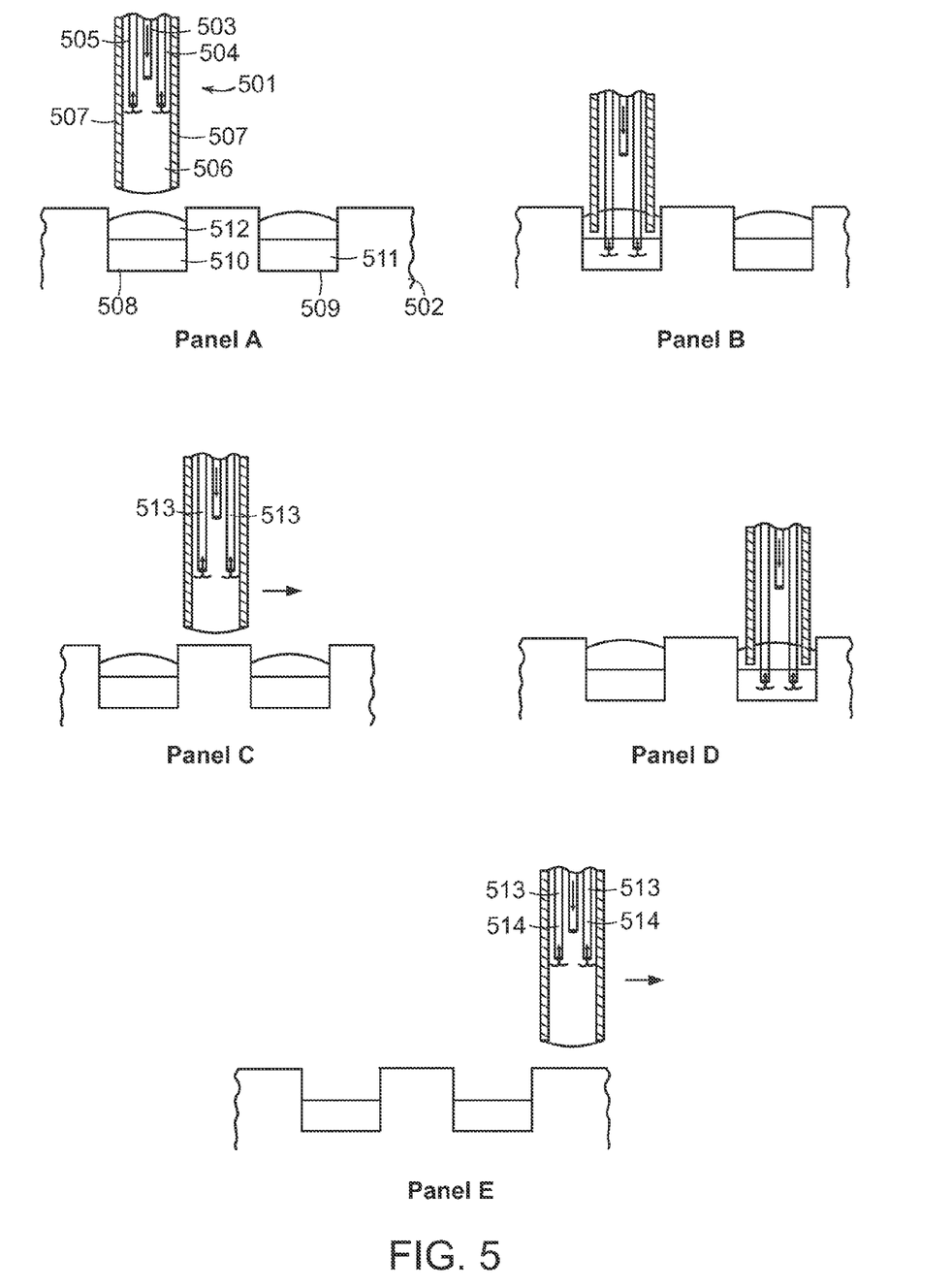
FIG. 5, panels A to E are drawings depicting an embodiment of a system having a sampling member and a vessel, and also depict interaction of the sampling member and the vessel.

FIG. 5 depicts a system 500 including a sampling device 501 and a vessel 502, and shows interaction of the sampling device 501 and the vessel 502 for acquisition and/or dispensing of samples (FIG. 5, panel A). The sampling device 501 includes an outer sheath 507; and a plurality of tubes within the sheath. In FIG. 5, device 501 is shown with two tubes 504 and 505 that acquire a sample. However, device 501 can be configured with only a single tube for sample acquisition, or can be configured with more than two tubes for sample acquisition, e.g., 3 tubes, 4 tubes, 5 tubes, 10 tubes, 15 tubes, 20 tubes, 50 tubes, etc. In FIG. 5, device 501 is shown with one tube 503 that expels a fluid that is immiscible with the sample. However, device 501 can be configured with more than one tube that expels a fluid that is immiscible with the sample, e.g., 3 tubes, 4 tubes, 5 tubes, 10 tubes, 15 tubes, 20 tubes, 50 tubes, etc. In embodiments in which the vessel 502 is a plate, for example a 96 well or 384 microtiter plate, the device 501 can be configured with 24 tubes for sample acquisition. In this embodiment, the outer diameter of the sample acquisition tubes is 0.3 mm and the diameter of the outer sheath is 2.5 mm.

In device 501, the tubes that acquires the sample 504 and 505 are extendable beyond a distal end of the sheath and retractable to within the sheath. FIG. 5, panel A shows the sample acquisition tubes 504 and 505 retracted within the outer sheath 507.

The outer sheath and the plurality of tubes can be of any shape, for example, a cylinder, a regular polygon, or an irregular polygon. The shape of the outer sheath is independent of the shape of the plurality of tubes. The outer sheath and the plurality of tubes can be made of any material suitable to interact with biological or chemical species. Exemplary materials include TEFLON (commercially available from Dupont, Wilmington, Del.), polytetrafluoroethylene (PTFE; commercially available from Dupont, Wilmington, Del.), polymethyl methacrylate (PMMA; commercially available from TexLoc, Fort Worth, Tex.), polyurethane (commercially available from TexLoc, Fort Worth, Tex.), polycarbonate (commercially available from TexLoc, Fort Worth, Tex.), polystyrene (commercially available from TexLoc, Fort Worth, Tex.), polyetheretherketone (PEEK; commercially available from TexLoc, Fort Worth, Tex.), perfluoroalkoxy (PFA; commercially available from TexLoc, Fort Worth, Tex.), or Fluorinated ethylene propylene (FEP; commercially available from TexLoc, Fort Worth, Tex.).

The vessel 502, can be any type of vessel that is suitable for holding a sample. Exemplary vessels include plates (e.g., 96 well or 384 well plates), eppendorf tubes, vials, beakers, flasks, centrifuge tubes, capillary tubes, cryogenic vials, bags, cups, or containers. The vessel can be made of any material suitable to interact with biological or chemical species. Exemplary materials include TEFLON (commercially available from Dupont, Wilmington, Del.), polytetrafluoroethylene (PTFE; commercially available from Dupont, Wilmington, Del.), polymethyl methacrylate (PMMA; commercially available from TexLoc, Fort Worth, Tex.), polyurethane (commercially available from TexLoc, Fort Worth, Tex.), polycarbonate (commercially available from TexLoc, Fort Worth, Tex.), polystyrene (commercially available from TexLoc, Fort Worth, Tex.), polyetheretherketone (PEEK; commercially available from TexLoc, Fort Worth, Tex.), perfluoroalkoxy (PFA; commercially available from TexLoc, Fort Worth, Tex.), or Fluorinated ethylene propylene (FEP; commercially available from TexLoc, Fort Worth, Tex.).

In this figure, the vessel is a plate having wells 508 and 509. The bottom portion of each well is filled with samples 510 and 511, and the remaining portion of each well 508 and 509 is filled with an overlay of a fluid 512 that is immiscible with the samples 510 and 511. The immiscible fluid 512 is the same fluid that is expelled by the immiscible fluid tube 503.

The system 500 is primed by continuously flowing the immiscible fluid 512 out of the tube 503 that expels the immiscible fluid, while sampling tubes 504 and 505 continuously intake the immiscible fluid. Flow rates of the immiscible fluid are controlled by a fluid controller, e.g., a PC running WinPumpControl software (Open Cage Software, Inc., Huntington, N.Y.), connected to at least one pump. An exemplary pump is shown in Davies et al. (WO 2007/091229). Other commercially available pumps can also be used. Exemplary flow rates range from about 1 µl/min to about 100 µl/min. An exemplary flow rate is about 1 µl/min, 3 µl/min, 5 µl/min, 10 µl/min, 20 µl/min, 30 µl/min, 50 µl/min, 70 µl/min, 90 µl/min, 95 µl/min, or about 100 µl/min.

In certain embodiments, flow is controlled such that the flow rate out of the tube 503 that continuously expels the immiscible fluid 512 is the same or similar to the total intake flow rate of sample acquisition tubes 504 and 505. For example, the flow rate out of tube 503 can range from about 2 µl/min to about 100 µl/min, while the intake flow rate for each of sample acquisition tubes 504 and 505 can range from about 1 µl/min to about 50 µl/min. Exemplary flow rates are as follows: flow rate of 2 µl/min expelled from tube 503, with an intake flow rate for each of sample acquisition tubes 504 and 505 of 1 µl/min; flow rate of 6 µl/min expelled from tube 503, with an intake flow rate for each of sample acquisition tubes 504 and 505 of 3 µl/min; flow rate of 10 µl/min expelled from tube 503, with an intake flow rate for each of sample acquisition tubes 504 and 505 of 5 µl/min; flow rate of 20 µl/min expelled from tube 503, with an intake flow rate for each of sample acquisition tubes 504 and 505 of 10 µl/min; and flow rate of 100 µl/min expelled from tube 503, the intake flow rate for each of sample acquisition tubes 504 and 505 is 50 µl/min.

Alternatively, the flow rate out of tube 503 is greater than the total intake flow rate of sample acquisition tubes 504 and 505. For example, the flow rate out of tube 503 can range from about 5 µl/min to about 100 µl/min, while the intake flow rate for each of sample acquisition tubes 504 and 505 can range from about 1 µl/min to about 95 µl/min. Exemplary flow rates are as follows: flow rate of 6 µl/min expelled from tube 503, with an intake flow rate for each of sample acquisition tubes 504 and 505 of 2 µl/min; flow rate of 10 µl/min expelled from tube 503, with an intake flow rate for each of sample acquisition tubes 504 and 505 of 4 µl/min; flow rate of 20 µl/min expelled from tube 503, with an intake flow rate for each of sample acquisition tubes 504 and 505 of 8 µl/min; and flow rate of 100 µl/min expelled from tube 503, with an intake flow rate for each of sample acquisition tubes 504 and 505 of 48 µl/min. In this regard, a slightly greater amount of immiscible fluid is expelled into the outer sheath than is taken in by the sample acquisition tubes. Thus, a lower portion of the outer sheath 506 is continuously filled with the immiscible fluid 512, and distal portions of sample acquisition tubes 504 and 505 are continuously immersed in the immiscible fluid.

The system is primed when a lower portion 506 of the outer sheath 507 is filled with the immiscible fluid 512, and distal portions of sample acquisition tubes 504 and 505 are continuously immersed in the immiscible fluid 512.

Now primed, the sampling device 501 is extended into well 508 to acquire an amount of sample 510 (FIG. 5, panel B). The outer sheath 507 is lowered into the overlay of immiscible fluid 512, and does not contact sample 510 (FIG. 5, panel B). Sampling tubes 504 and 505 extend into the sample 510 (FIG. 5, panel B). Sample 510 can be any type of biological or chemical species. In certain embodiments, the sample is a gene or gene product from a biological organism. In other embodiments, the sample includes PCR reagents. Once a sufficient amount of sample 510 has been acquired, sampling tubes 504 and 505 are retracted from sample 510 in well 508, and return to within the outer sheath 507 (FIG. 5, panel C).

Once sampling tubes 504 and 505 have retracted to within the outer sheath 507, the outer sheath 507 retracts from the immiscible fluid 512 in well 508 (FIG. 5, panel C). Sampling device 501 then proceeds to move to the next well 509 containing a sample 511 (FIG. 5, panel C). As sampling device 501 moves to the next well 509, acquired sample 513 continues to move through sampling device 501 (FIG. 5, panel C). Additionally, tube 503 continues to expel the immiscible fluid 512, sampling tubes 504 and 505 continue to intake the immiscible fluid 512, and the lower portion 506 of the outer sheath 507 remains continuously filled with the immiscible fluid (FIG. 5, panel C). Thus the distal portions of sampling tubes 504 and 505 remain continuously immersed in the immiscible fluid and do not contact the atmosphere (FIG. 5, panel C). Thus, a sample is acquired without the system taking in any gas.

Once positioned above the well 509, the sampling device 501 is extended into well 509 to acquire an amount of sample 511 (FIG. 5, panel D). The outer sheath 507 is lowered into the overlay of immiscible fluid 512, and does not contact sample 511 (FIG. 5, panel D). Sampling tubes 504 and 505 extend into the sample 511 (FIG. 5, panel D). Sample 511 can be any type of biological or chemical species. In certain embodiments, the sample is a gene or gene product from a biological organism. In other embodiments, the sample includes PCR reagents. Once a sufficient amount of sample 511 has been acquired, sampling tubes 504 and 505 are retracted from sample 511 in well 509, and return to within the outer sheath 507 (FIG. 5, panel D).

Once sampling tubes 504 and 505 have retracted to within the outer sheath 507, the outer sheath 507 retracts from the immiscible fluid 512 in well 509 (FIG. 5, panel E). Sampling device 501 then proceeds to move to the next well containing a sample (FIG. 5, panel E). As sampling device 501 moves to the next well, acquired sample 514 continues to move through sampling device 501 (FIG. 5, panel E). Acquired sample 513 and acquired sample 514 are separated by the immiscible fluid 512. Additionally, tube 503 continues to expel the immiscible fluid 512, sampling tubes 504 and 505 continue to intake the immiscible fluid 512, and the lower portion 506 of the outer sheath 507 remains continuously filled with the immiscible fluid (FIG. 5, panel E). Thus the distal portions of sampling tubes 504 and 505 remain continuously immersed in the immiscible fluid and do not contact the atmosphere (FIG. 5, panel E). Thus, samples are acquired without the system taking in any gas. The process repeats until the desired number of samples have been acquired. Because samples within a vessel or within separate vessels are separated by the immiscible fluid, there is no carry-over or cross contamination between samples in a vessel and between samples in different vessels.

The sampling device 501 is controlled by at least one robotics system. A first robotics system controls movement of the sampling device 501 between sample wells and movement of the outer sheath 507 during sample acquisition. A second robotics system controls the sampling tubes 503 and 504 for extension from the outer sheath 507 and retraction into the outer sheath 507. At least one pump is connected to the tube 503 that expels the immiscible fluid, and at least one pump is connected to the sample acquisition tubes 503 and 504. An exemplary pump is shown in Davies et al. (WO 2007/091229). Other commercially available pumps can also be used. The pump connected to tube 503 obtains the immiscible fluid from a reservoir that is fluidly connected to the pump. The pumps are controlled by a flow controller, e.g., a PC running WinPumpControl software (Open Cage Software, Inc., Huntington, N.Y.), for control of direction of flow and flow rates.

Sampling system 500 can be fluidly connected, e.g., tubes or channels, to an type of analysis device. In certain embodiments, the sampling system 500 is connected to a liquid bridge system, as shown in Davies et al. (WO 2007/091228). The liquid bridge system can be connected to a thermocycler to perform PCR reactions on the acquired sample. An exemplary thermocycler and methods of fluidly connecting a thermocycler to a liquid bridge system are shown in Davies et al. (WO 2005/023427, WO 2007/091230, and WO 2008/038259). The thermocycler can be connected to an optical detecting device to detect the products of the PCR reaction. An optical detecting device and methods for connecting the device to the thermocycler are shown in Davies et al. (WO 2007/091230 and WO 2008/038259).

INCORPORATION BY REFERENCE AND EQUIVALENTS

References and citations to other documents, such as patents, patent applications, patent publications, journals, books, papers, web contents, have been made throughout this disclosure. All such documents are hereby incorporated herein by reference in their entirety for all purposes. Various modifications of the invention and many further embodiments thereof, in addition to those shown and described herein, will become apparent to those skilled in the art from the full contents of this document, including the references to the scientific and patent literature cited herein.

What is claimed is:

1. A sampling device comprising:
   an outer sheath comprising a distal end on a lower portion of the outer sheath;
   a plurality of tubes within the outer sheath, the plurality comprising at least one immiscible fluid supply tube;
   at least one actuatable sample tube comprising a distal end proximate the lower portion of the outer sheath, wherein the at least one actuatable sample tube is within the outer sheath and is substantially parallel to the plurality of tubes within the outer sheath;
   at least one pump in operable communication with the at least one actuatable sample tube, the at least one immiscible fluid supply tube, or both;

at least one immiscible fluid supply source in fluid communication with the at least one immiscible fluid supply tube; and at least one actuator operably associated with the at least one actuatable sample tube and configured to extend the distal end of the at least one actuatable sample tube beyond the distal end of the outer sheath and retract the distal end of the at least one actuatable sample tube to within the outer sheath, wherein the device is configured to provide counter-flow between the immiscible fluid supply tube and the at least one actuatable sample tube.

2. The device according to claim 1, wherein the at least one sample tube and at least one immiscible fluid supply tube are in fluid communication with one another and the device is configured to provide a counter-flow of an immiscible fluid between the immiscible fluid supply tube and the at least one actuatable sample tube.

3. The device according to claim 2, wherein the at least one immiscible fluid supply tube is configured to continuously expel immiscible fluid from the immiscible fluid supply source.

4. The device according to claim 3, wherein the at least one actuatable sample tube is configured to envelope the sample within the immiscible fluid.

5. The device according to claim 1, wherein the at least one actuatable sample tube is configured to acquire a sample without the introduction of a non-dissolved gas into the at least one actuatable sample tube that acquires the sample.

6. The device according to claim 1, wherein the device is in fluid communication with a liquid bridge system.

7. A system for sample acquisition comprising:
a sampling device comprising
an outer sheath comprising a distal end on a lower portion of the outer sheath;
a plurality of tubes within the outer sheath, the plurality of tubes comprising at least one immiscible fluid supply tube; and
at least one actuatable sample tube having a distal end proximate the lower portion of the outer sheath, wherein the at least one actuatable sample tube is within the outer sheath and is substantially parallel to the plurality of tubes within the outer sheath;

at least one pump in operable communication with the at least one actuatable sample tube, the at least one immiscible fluid supply tube, or both;

at least one immiscible fluid supply source in fluid communication with the at least one immiscible fluid supply tube; and at least one actuator operably associated with the at least one actuatable sample tube and configured to extend tile distal end of the at least one actuatable sample tube beyond tile distal end of the outer sheath and retract the distal end of the at least one actuatable sample tube to be within the outer sheath;

at least one vessel configured for containment of a sample and all overlay of a fluid that is immiscible with the sample; and wherein the distal end of the outer sheath and the distal end of the at least one actuatable sample tube are configured to interact with the at least one vessel to acquire the sample without also acquiring a non-dissolved gas, wherein the device is configured to provide counter-flow between the immiscible fluid supply tube and the at least one actuatable sample tube.

8. The system according to claim 7, wherein a counter-flow exists between the at least one actuatable sample tube and the at least one immiscible fluid and the tube that acquires the sample supply tube.

9. The system according to claim 8, wherein the at least one immiscible fluid supply tube is configured to continuously expel the immiscible fluid.

10. The system according to claim 9, wherein the at least one actuatable sample tube is configured to envelope a sample within the immiscible fluid.

11. The system according to claim 7, further comprising at least one robotics system configured to control movement of the sampling device, and configured to control movement of the at least one actuatable sample tube.

12. The system according to claim 11, wherein the at least one pump comprises a first pump connected to the at least one actuatable sample tube, and a second pump connected to the at least one immiscible fluid supply tube that.

13. The system according to claim 7, further comprising a liquid bridge that is in fluid contact communication with continuously the sampling device.

* * * * *

UNITED STATES PATENT AND TRADEMARK OFFICE
CERTIFICATE OF CORRECTION

PATENT NO. : 8,697,011 B2  
APPLICATION NO. : 12/468367  
DATED : April 15, 2014  
INVENTOR(S) : David McGuire et al.

Page 1 of 1

It is certified that error appears in the above-identified patent and that said Letters Patent is hereby corrected as shown below:

Title page, item (75) Inventors: "Curtain" should read as --Curtin--

Signed and Sealed this  
Twenty-seventh Day of October, 2015

Michelle K. Lee  
*Director of the United States Patent and Trademark Office*